United States Patent
Höglund

(10) Patent No.: US 10,004,536 B2
(45) Date of Patent: Jun. 26, 2018

(54) MEDICAL DEVICE

(71) Applicant: RESORBABLE DEVICES AB, Uppsala (SE)

(72) Inventor: Odd Höglund, Uppsala (SE)

(73) Assignee: RESORBABLE DEVICES AB, Uppsala (SE)

( * ) Notice: Subject to any disclaimer, the term of this patent is extended or adjusted under 35 U.S.C. 154(b) by 0 days. days.

(21) Appl. No.: 15/325,186

(22) PCT Filed: Jul. 6, 2015

(86) PCT No.: PCT/SE2015/050798
§ 371 (c)(1),
(2) Date: Jan. 10, 2017

(87) PCT Pub. No.: WO2016/007078
PCT Pub. Date: Jan. 14, 2016

(65) Prior Publication Data
US 2017/0172625 A1    Jun. 22, 2017

(30) Foreign Application Priority Data

Jul. 11, 2014 (SE) ...................................... 1450890
Jul. 11, 2014 (SE) ...................................... 1550175

(51) Int. Cl.
*A61B 17/70* (2006.01)
*A61B 17/68* (2006.01)
(Continued)

(52) U.S. Cl.
CPC .............. *A61B 17/68* (2013.01); *A61B 17/12* (2013.01); *A61B 17/12009* (2013.01);
(Continued)

(58) Field of Classification Search
CPC ... Y10T 24/152; Y10T 24/14; Y10T 24/1498; G01B 7/16; B65D 63/10; B65D 63/14;
(Continued)

(56) References Cited

U.S. PATENT DOCUMENTS 3,078,532 A * 2/1963 Bywater ............... F16L 33/035
24/22
3,292,961 A * 12/1966 Moberg ............... B65D 77/185
24/30.5 R
(Continued)

FOREIGN PATENT DOCUMENTS

DE      202008008960 U1    9/2008
EP         0045164 A1     2/1982
(Continued)

OTHER PUBLICATIONS

Official Action dated Mar. 15, 2018 from corresponding European Patent Application No. 15818515.7.

*Primary Examiner* — Ellen C Hammond
*Assistant Examiner* — Stuart S Bray
(74) *Attorney, Agent, or Firm* — Porter Wright Morris & Arthur LLP

(57) ABSTRACT

A medical device (100) comprises an elongated, flexible band (110) having a front side (112), a rear side (114), a leading end (116) and a trailing end (118), and having perforations (120) and rungs (122) defined therein. A locking case (130, 132) is arranged on the front side (112) of the band (112) and has a channel (150) dimensioned for reception of the band (110). The medical device (100) also comprises a locking member (140, 142, 144) configured to interlock perforations (120) and rungs (122) defined in the band (110). Multiple studs (160, 162) are arranged on the rear side (114) of the band (110).

13 Claims, 7 Drawing Sheets

(51) Int. Cl.
  *A61B 17/82* (2006.01)
  *A61B 17/12* (2006.01)
  *A61B 17/132* (2006.01)
  *A61F 6/20* (2006.01)
  *F16L 3/233* (2006.01)
  *A61B 17/00* (2006.01)
  *B65D 63/10* (2006.01)

(52) U.S. Cl.
  CPC .......... *A61B 17/1322* (2013.01); *A61B 17/82* (2013.01); *A61B 2017/00004* (2013.01); *A61F 6/202* (2013.01); *B65D 63/10* (2013.01); *B65D 2563/106* (2013.01); *F16L 3/2332* (2013.01); *Y10T 24/14* (2015.01)

(58) Field of Classification Search
  CPC . B65D 63/16; B65D 63/1027; B65D 63/1036
  See application file for complete search history.

(56) References Cited

U.S. PATENT DOCUMENTS

| | | | | |
|---|---|---|---|---|
| 3,867,944 A * | 2/1975 | Samuels | ............... | A61B 17/122 24/23 W |
| 3,943,606 A * | 3/1976 | Ernst | ................... | A22C 15/002 24/3.1 |
| 4,146,022 A * | 3/1979 | Johnson | ............. | A61B 17/8861 606/103 |
| 4,183,119 A * | 1/1980 | Stewart | ............. | B65D 63/1063 24/16 PB |
| 4,347,648 A * | 9/1982 | Dekkers | ............. | B65D 63/1063 24/16 PB |
| 4,730,615 A * | 3/1988 | Sutherland | ........... | A61B 17/823 24/16 PB |
| 4,813,416 A * | 3/1989 | Pollak | .................... | A61B 17/04 24/16 PB |
| 4,991,266 A * | 2/1991 | Oetiker | ................ | F16L 33/035 24/20 CW |
| 5,135,188 A * | 8/1992 | Anderson | ......... | B65D 63/1063 24/16 PB |
| 5,366,461 A * | 11/1994 | Blasnik | ................ | A61B 17/823 24/20 CW |
| 5,766,218 A * | 6/1998 | Arnott | ................... | A61B 17/823 24/16 PB |
| 5,810,854 A * | 9/1998 | Beach | ................. | A61B 17/0401 24/16 PB |
| 5,832,567 A * | 11/1998 | Edwards | ............ | B65D 63/1027 24/16 PB |
| 5,924,171 A * | 7/1999 | Sorensen | ........... | B65D 63/1063 24/16 PB |
| 6,105,210 A * | 8/2000 | Benoit | ............... | B65D 63/1063 24/16 PB |
| 6,185,791 B1 * | 2/2001 | Khokhar | ............ | B65D 63/1063 24/16 PB |
| 6,253,421 B1 * | 7/2001 | Kraus | ................ | B65D 63/1063 24/16 PB |
| 6,279,203 B1 * | 8/2001 | Hundley | ............ | B65D 63/1036 24/16 PB |
| 6,372,068 B1 * | 4/2002 | Kincel | .................... | B29C 66/69 156/308.2 |
| 7,062,820 B1 * | 6/2006 | Oestreich | ............. | B65D 63/1027 24/16 PB |
| 8,460,295 B2 * | 6/2013 | McClellan | ........... | A61B 17/823 606/215 |
| 8,506,597 B2 * | 8/2013 | Kaiser | ................... | A61B 17/56 606/232 |
| 8,936,621 B2 * | 1/2015 | Denham | ............. | A61B 17/0401 606/228 |
| 9,315,142 B1 * | 4/2016 | Pedrini | .................. | B65D 63/10 |
| 9,326,807 B2 * | 5/2016 | Schaller | ............. | A61B 17/8861 |
| 9,398,903 B2 * | 7/2016 | McClellan | ......... | A61B 17/0401 |
| 9,474,553 B2 * | 10/2016 | Koch | ..................... | A61B 17/685 |
| 9,539,004 B2 * | 1/2017 | McClellan | ........ | A61B 17/06166 |
| 9,643,763 B2 * | 5/2017 | Kierstead | ............ | B65D 63/1027 |
| 9,718,225 B2 * | 8/2017 | Luo | ...................... | B29C 45/0005 |
| 9,802,743 B2 * | 10/2017 | Foreman | ............. | B65D 63/1072 |
| 2002/0083559 A1 * | 7/2002 | Hatch | ................. | B65D 63/1027 24/16 PB |
| 2002/0170151 A1 * | 11/2002 | Caveney | ............. | B65D 63/1036 24/16 PB |
| 2002/0170152 A1 * | 11/2002 | Caveney | ............. | B65D 63/1036 24/16 PB |
| 2002/0170153 A1 * | 11/2002 | Brownlee | .......... | B65D 63/1036 24/16 PB |
| 2003/0029004 A1 * | 2/2003 | Berrocal | ............. | B65D 63/1063 24/16 PB |
| 2004/0045960 A1 * | 3/2004 | Rose | ......................... | H02G 3/08 220/3.9 |
| 2005/0062608 A1 * | 3/2005 | Costa | ...................... | B65D 55/08 340/572.9 |
| 2005/0204515 A1 * | 9/2005 | Hewes | ................ | B65D 63/1063 24/16 PB |
| 2005/0262672 A1 * | 12/2005 | Okamoto | ........... | B65D 63/1063 24/716 |
| 2006/0168767 A1 * | 8/2006 | Huang | ................ | B65D 63/1027 24/16 PB |
| 2006/0235468 A1 * | 10/2006 | Huitema | .............. | A61B 17/064 606/219 |
| 2007/0028426 A1 * | 2/2007 | Laporte | .............. | B65D 63/1063 24/16 PB |
| 2009/0281560 A1 | 11/2009 | Wexner et al. | | |
| 2010/0125981 A1 * | 5/2010 | Ritola | .................... | B65D 63/08 24/265 EC |
| 2010/0212117 A1 * | 8/2010 | Haase | ................. | B65D 63/1027 24/16 PB |
| 2011/0131768 A1 * | 6/2011 | Watson | ............... | B65D 63/1063 24/16 PB |
| 2011/0167594 A1 | 7/2011 | Gmeilbauer | | |
| 2012/0084948 A1 * | 4/2012 | Breen, IV | .......... | B65D 63/1063 24/16 R |
| 2012/0210541 A1 * | 8/2012 | Koncelik, Jr. | ..... | B65D 63/1018 24/21 |
| 2012/0272485 A1 * | 11/2012 | Liang | ................. | B65D 63/1072 24/16 PB |
| 2013/0092803 A1 * | 4/2013 | Fujiwara | ............. | B60R 16/0215 248/74.2 |
| 2013/0298353 A1 * | 11/2013 | Drane | ................ | B65D 63/1063 24/16 PB |
| 2013/0333163 A1 * | 12/2013 | Chen | .................. | B65D 63/1081 24/16 PB |
| 2015/0013555 A1 * | 1/2015 | Nakajima | ............. | B65D 63/16 100/33 R |
| 2016/0001943 A1 * | 1/2016 | Harsley | ................. | F16L 3/2336 24/16 PB |
| 2016/0214776 A1 * | 7/2016 | King | ................... | B65D 63/1072 |
| 2016/0223100 A1 * | 8/2016 | Geiger | .................... | F16L 3/137 |
| 2016/0280433 A1 * | 9/2016 | Montejo | ................ | B65D 63/16 |
| 2017/0050786 A1 * | 2/2017 | Kozminkse | ........ | B65D 63/1027 |
| 2017/0066578 A1 * | 3/2017 | Kierstead | ............. | B65D 63/14 |
| 2017/0088322 A1 * | 3/2017 | Reinke | ............... | B65D 63/1027 |
| 2017/0240327 A1 * | 8/2017 | Sanders | ............... | B65D 63/18 |
| 2017/0313484 A1 * | 11/2017 | Na | ...................... | B65D 63/1027 |
| 2017/0328700 A1 * | 11/2017 | Murphy | ................. | G01B 7/16 |
| 2017/0351224 A1 * | 12/2017 | Reece | ................. | G04G 13/026 |
| 2018/0002544 A1 * | 1/2018 | Gao | ..................... | C09D 5/4419 |

FOREIGN PATENT DOCUMENTS

WO 2007/010092 A1 1/2007
WO 2014/007719 A1 1/2014

* cited by examiner

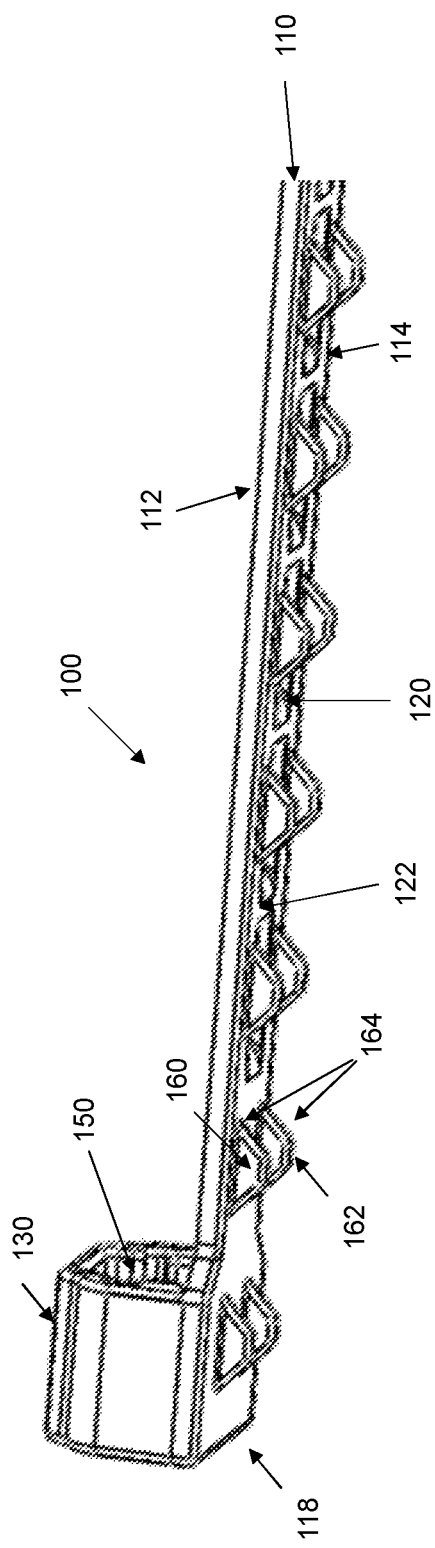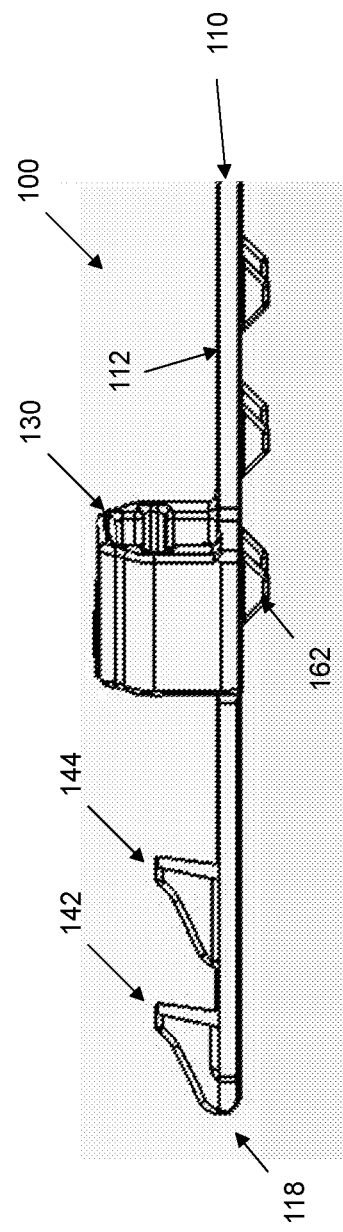

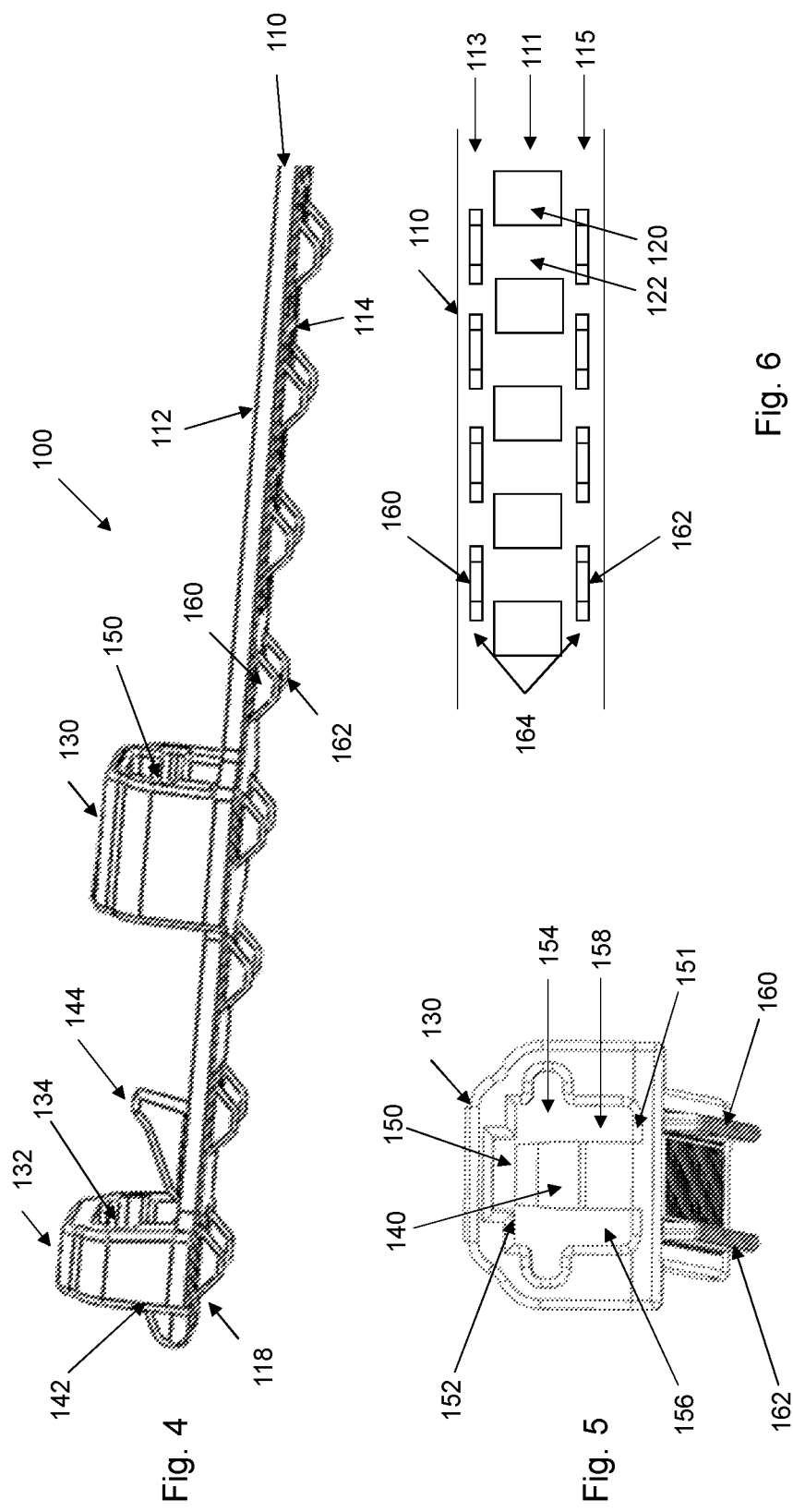

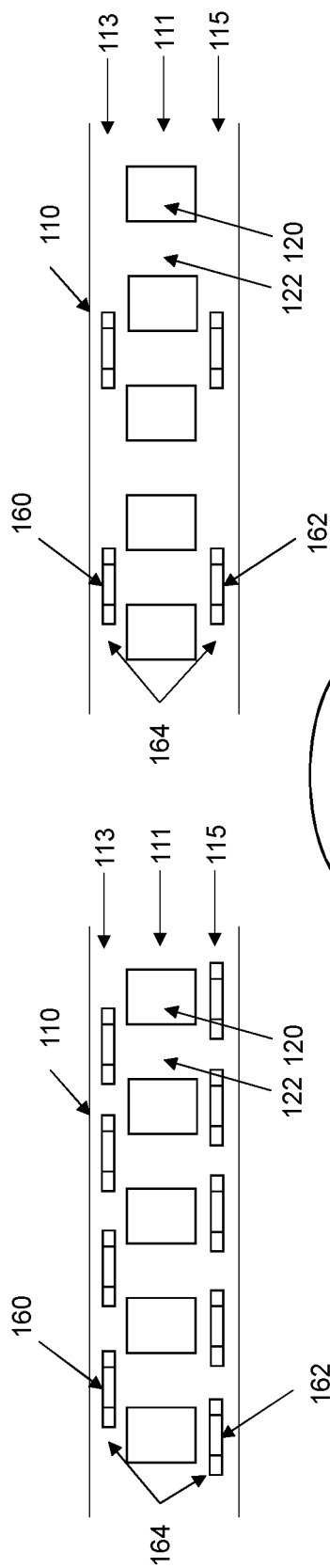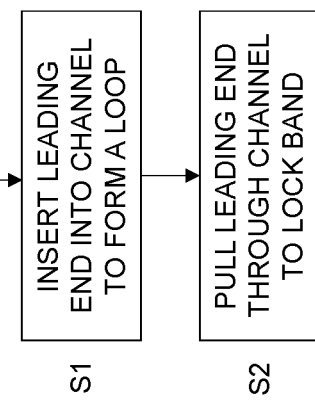

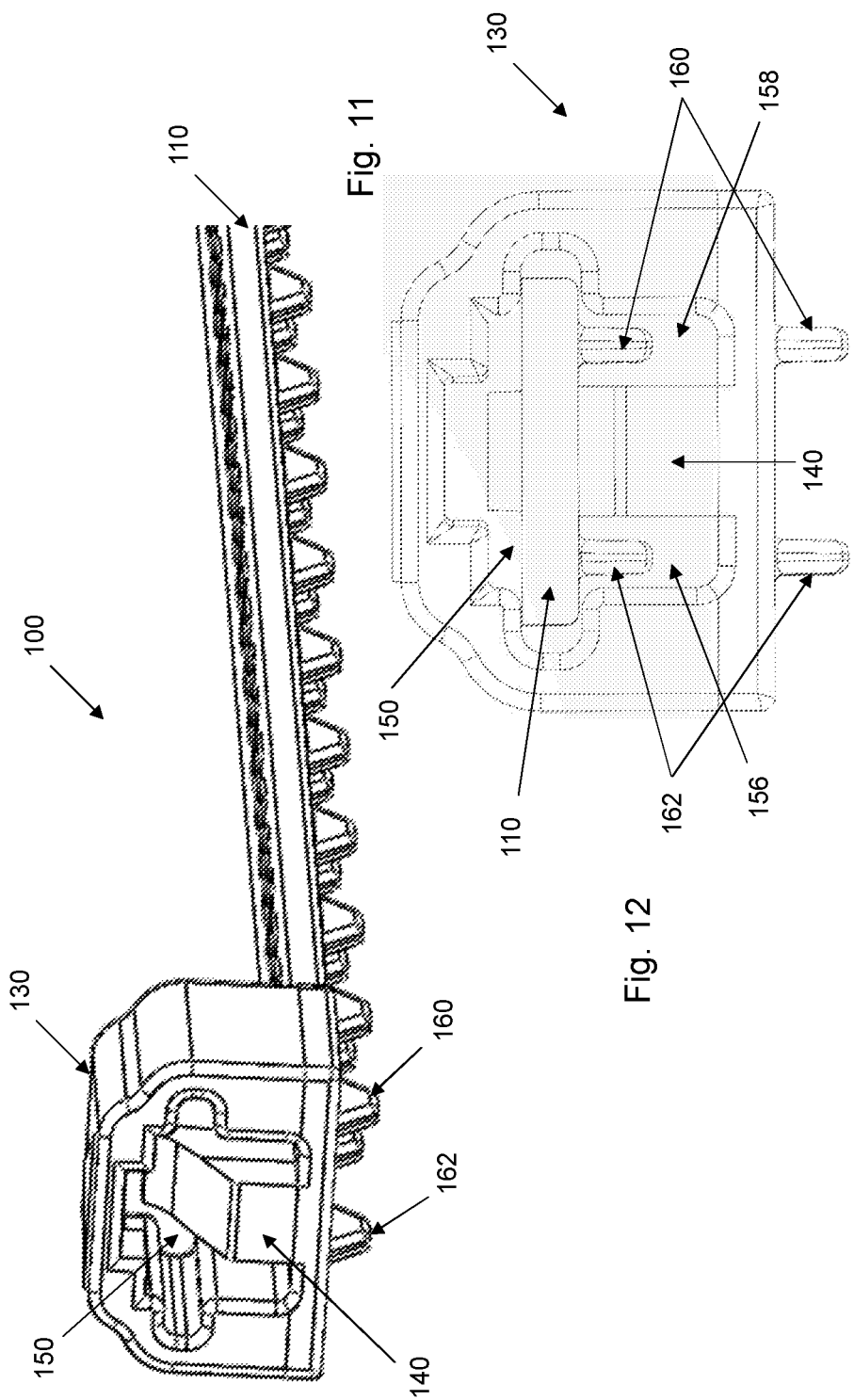

MEDICAL DEVICE

TECHNICAL FIELD

The present embodiments generally relate to medical devices, and in particular to such medical device based on the principle of cable ties.

BACKGROUND

Bone fractures are sometimes fixated or stabilized using plates attached to the fractured bone by means of surgical nails or screws. This procedure generally works well for most patients. However, some patients have weak or brittle bones, for instance osteoporotic patients. In such patients, surgical nails or screws can often not be used to attach the plates onto the fractured bones. Hence, alternative procedures are needed for internal fixation of fractured bones in osteoporotic patients and other patients suffering from weak or brittle bones.

A common alternative to surgical nails or screws is cerclage, which is an orthopedic procedure in which the ends of an oblique bone fracture are bound together with wire loops or metal or plastic bands, in combination with an intramedullary pin, to hold them in position until the fracture has healed. The wire or band is generally very thin and may be cumbersome to handle for the surgeon. Furthermore, the wire or band needs to be held tight against the fractured bone in order to prevent any movement between the intramedullary pin and the bone and/or between the fractured bone parts. However, it is not uncommon, when tightening the wire or band, to unintentionally break the wire or band.

Another problem with the wires or bands used in cerclage procedures is that they effectively restrict microcirculation in the periosteum of the fractured bone. U.S. Pat. No. 4,146,022 discloses implants that can be used together with metal wires for internal fixation of bone fractures. Each implant is essentially a stainless steel cylindrical body having four sharp point at one end to be inserted into the bone tissue (cortex of the bone). A circular axial bore extends through the cylindrical body and a diametrical groove is present across the other end of the cylindrical body. A metal wire is then wrapped around the bone and positioned in the respective grooves in the top of each implant. The wire loop is tightened and will be elevated from the bone surface by the implants.

The implants of U.S. Pat. No. 4,146,022 are still marred by the problems of handling the metal wire and tightening it around the bone without breaking the metal wire. A further shortcoming of the implants is that a second surgical procedure is needed after bone healing in order to remove the implants and the wire loops.

Thus, there is a need for a medical device that solves at least some of the shortcomings of prior art technology.

SUMMARY

It is a general objective to provide a medical device solving at least some of the shortcomings of prior art technology.

This and other objectives are met by embodiments disclosed herein.

An aspect of the embodiments relates to a medical device comprising an elongated, flexible band having a front side, a rear side, a leading end and a trailing end, and having perforations and rungs defined therein. A locking case is arranged on the front side of the band and has a channel dimensioned for reception of the band. The medical device also comprises a locking member configured to interlock perforations and rungs defined in the band. Multiple studs are arranged on the rear side of the band.

Another aspect of the embodiments relates to a method of stabilizing a bone fracture. The method comprises inserting a leading end of a band of a medical device as defined above into a channel of a locking case of the medical device to form a loop around a fractured bone. The leading end of the band is pulled through the channel to lock the band around the fractured bone. Multiple studs arranged on a rear side of the band elevate the medical device from a surface of the fractured bone to reduce a risk of the medical device restricting microcirculation in periosteum of the fractured bone.

A further aspect of the embodiments relates to a tissue ligation method. The method comprises inserting a leading end of a band of a medical device as defined above into a channel of a locking case of the medical device to form a loop around a tissue. The leading end of the band is pulled through the channel to lock the band around the tissue and achieve a tissue ligation. Multiple studs arranged on a rear side of the band engage the tissue to reduce a risk of the medical device slipping off the tissue.

Yet another aspect of the embodiments relates to a pursestring suturing method. The method comprises inserting a leading end of a band of a medical device as defined above into a channel of a locking case of the medical device to form a loop encircling an opening of a tissue. The leading end of the band is pulled through the channel to lock said band around and closing the opening of the tissue. Multiple studs arranged on a rear side of the band engage the tissue to reduce a risk of the medical device slipping off said tissue.

BRIEF DESCRIPTION OF THE DRAWINGS

The embodiments, together with further objects and advantages thereof, may best be understood by making reference to the following description taken together with the accompanying drawings, in which:

FIG. 2 illustrates the locking case and a portion of the band of a medical device according to an embodiment;

FIG. 3 illustrates the locking case and a portion of the band of a medical device according to another embodiment;

FIG. 4 illustrates the locking case and a portion of the band of a medical device according to a further embodiment;

FIG. 5 schematically illustrates the channel in a locking case according to an embodiment;

FIG. 6 illustrates arrangement of studs on a band according to an embodiment;

FIG. 7 illustrates arrangement of studs on a band according to another embodiment;

FIG. 8 illustrates arrangement of studs on a band according to a further embodiment;

FIG. 9 is a flow chart illustrating method steps according to embodiments;

FIG. 11 schematically illustrates the locking case and a portion of the band of a medical device according to an embodiment;

FIG. 12 schematically illustrates the locking case having a band inserted into its channel.

DETAILED DESCRIPTION

Figure 1:
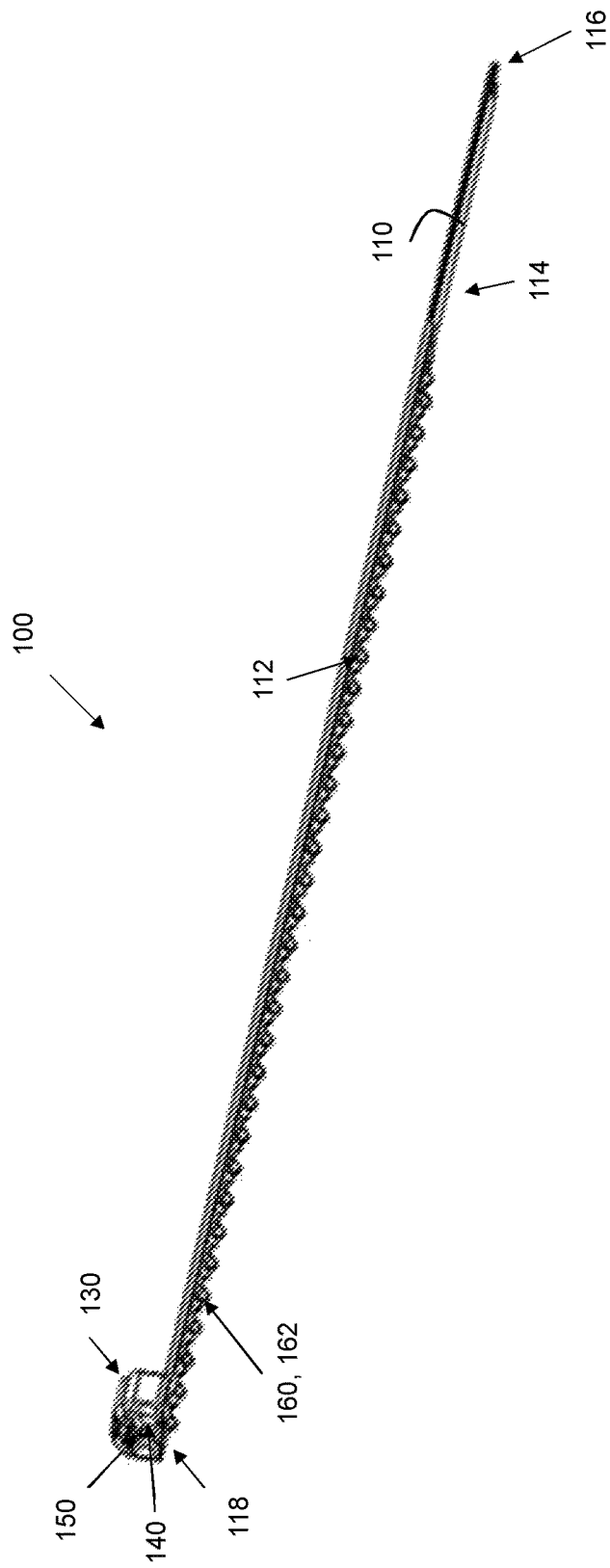
FIG. 1 is a schematic overview of a medical device according to an embodiment.

Throughout the drawings, the same reference numbers are used for similar or corresponding elements. The present embodiments generally relate to medical devices, and in particular to such medical devices based on the principle of cable ties. The medical devices of the embodiments can be used for various medical and surgical purposes in an animal body, such as a mammalian body, including a human body.

As an example, the medical device can efficiently be used instead of prior art cerclage and metal or plastic wires or bands when stabilizing a bone fracture, in particular for a patient having brittle or osteoporotic bones. The medical device of the embodiment has significant advantages over such prior art bone fracture stabilizing techniques. Firstly, the medical device can be handled by one hand of a medical person, leaving the other hand free for other purposes. Furthermore, the locking of the medical device is simplified and does not require tying any knots in the limited space where the surgical operation is taking place in the animal or human body. There is further hardly no risk of breaking the medical device in connection with locking it around the bone, which may happen during cerclage procedures when tightening a metal or plastic wire around the fractured bone. Furthermore, the medical device of the embodiments can achieve an efficient stabilization of a bone fracture while simultaneously allowing microcirculation in the periosteum and cortex of the fractured bone. Thus, the medical device does not restrict such microcirculation to the same degree as when tightening a metal or plastic wire around the fractured bone. This means that the medical device will preserve vascularity and microcirculation while achieving rigid fixation of the fractured bone and minimum trauma.

The medical device of the embodiments may also find other medical uses besides stabilization of fractured bones. For instance, the medical device can be used as a ligature for ligation of tissues and vessels in an animal body, such as a mammalian body, including a human body.

The medical device, ligature, of the embodiments has significant advantages over the prior art thread-based ligatures. Firstly, the medical device can be handled by one hand of a medical person, leaving the other hand free for lifting the tissue to be ligated slightly out from the surrounding body. Furthermore, the locking of the medical device is simplified and does not require tying any knots in the limited space where the surgical operation is taking place in the animal or human body. In addition, the medical device of the embodiments is designed to engage the tissue to be ligated to thereby reduce a risk of the medical device slipping off the tissue following the ligation procedure. Such slipping off is quite common in prior art technology generally requiring usage of extra or additional ligatures to secure tissue ligation if one of the ligature slips off the tissue.

The medical device may also be used as a purse-string suture, encircling an opening into a tissue and compressing the tissue, thereby closing the opening of the tissue. Placing a traditional purse-string suture around an opening of the tissue may be cumbersome if the tissue is difficult to access or during robotic surgery or traditional laparoscopic surgery. The medical device offers a standardized and simplified circular closure of an opening into tissues such as, but not restricted to, esophagus, stomach, small and large intestines. The medical device may therefore be used during the procedure to re-join intestines, anastomosis.

The medical device of the present embodiments is based on the principles of a cable tie (also denoted strap, zip tie, mouse belt, tie wrap, tie rap and quick draw in the art) for allowing forward motion of a band relative to a locking member but restricting or even fully preventing backward movement of the band relative to the locking member. This feature of cable tie, providing a reverse-motion brake, replaces the cumbersome operation of tying knots of metal or plastic wires and sutures/ligatures and thereby significantly simplifies the surgical procedure.

A general aspect of the embodiments relates to a medical device comprising an elongated, flexible band having a front side, a rear side, a leading end and a trailing end. The band further has perforations and rungs defined therein. The medical device also comprises a locking case arranged on the front side of the band and having a channel dimension for reception of the band. A locking member of the medical device is configured to interlock perforations and rungs defined in the band. The medical device further comprises multiple studs arranged on the rear side of the band.

The multiple studs arranged on the rear side of the band may have different advantages and uses depending on the particular application of the medical device.

In the case of stabilization of a fractured bone, the multiple studs will keep the band elevated from the surface of the fractured bone as the band is drawn through the locking case and locked around the fractured bone by the locking member. This means at this locked position the band is elevated a small distance from the surface of the fractured bone and will therefore not restrict blood vessels around the whole circumference of the fractured bone as prior art metal or plastic wires and bands used in cerlage procedures.

The multiple studs further have tissue engaging function, which means that when the band is tightened around tissue the multiple studs will engage and grip into the tissue. This implies that the multiple studs will reduce the risk for the medical device to move along the tissue or even slipping off the tissue.

Various embodiments of this aspect will now be further described in connection with the drawings.

Figure 13:
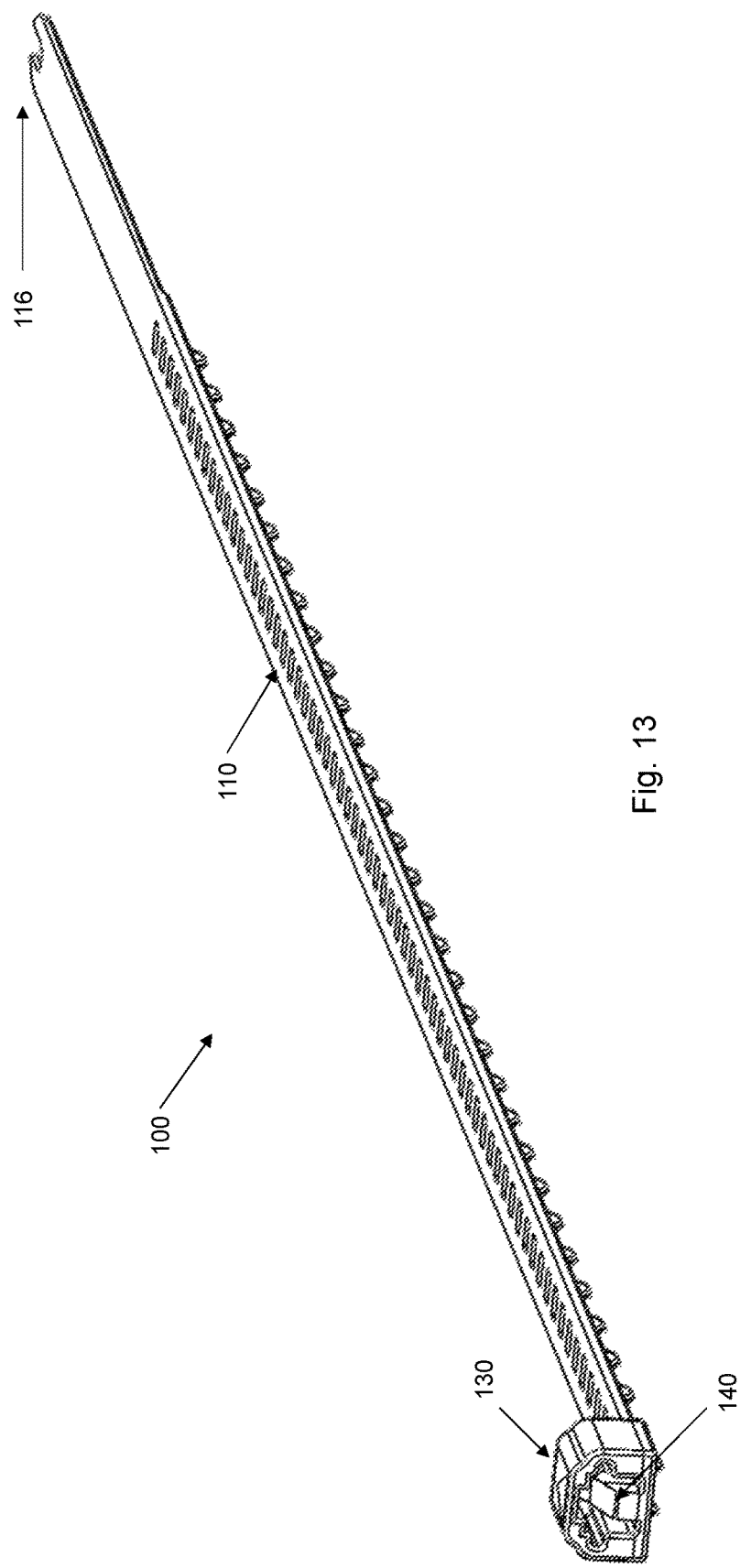
FIG. 13 is a schematic overview of a medical device according to an embodiment.

FIGS. 1 and 13 are illustrations of a particular embodiment of a medical device 100. The medical device 100 comprises an elongated, flexible band or strip 110 having a front side 112 and an opposite rear side 114. A locking case or head 130 is arranged on the front side 112 of the band, typically at or in connection with a trailing end 118 of the band 110. The opposite leading end 116 of the band 110 is adapted for insertion into a channel 150, through-hole or aperture running through the locking case 130.

The leading end 116 can be pointed for facilitating guiding of the band 110 into the channel 150. The leading end 116 could even be sharp to be able to penetrate tissue, when such a function is required. It is also possible to have a Y-shaped or forked leading end 116, which could facilitate introduction of the leading end 116 into the channel 150 of the locking case 130, see FIG. 13.

The reverse-motion brake action of the medical device 100 is achieved through perforations 120 and rungs 122, also denoted ratchet members in the art, provided in at least a portion of the band 110, see FIG. 2. The perforations 120 and rungs 122 are preferably arranged on at least the rear side 114 of the band 110 but could also, or instead, be present on the front side 112.

Figure 10:
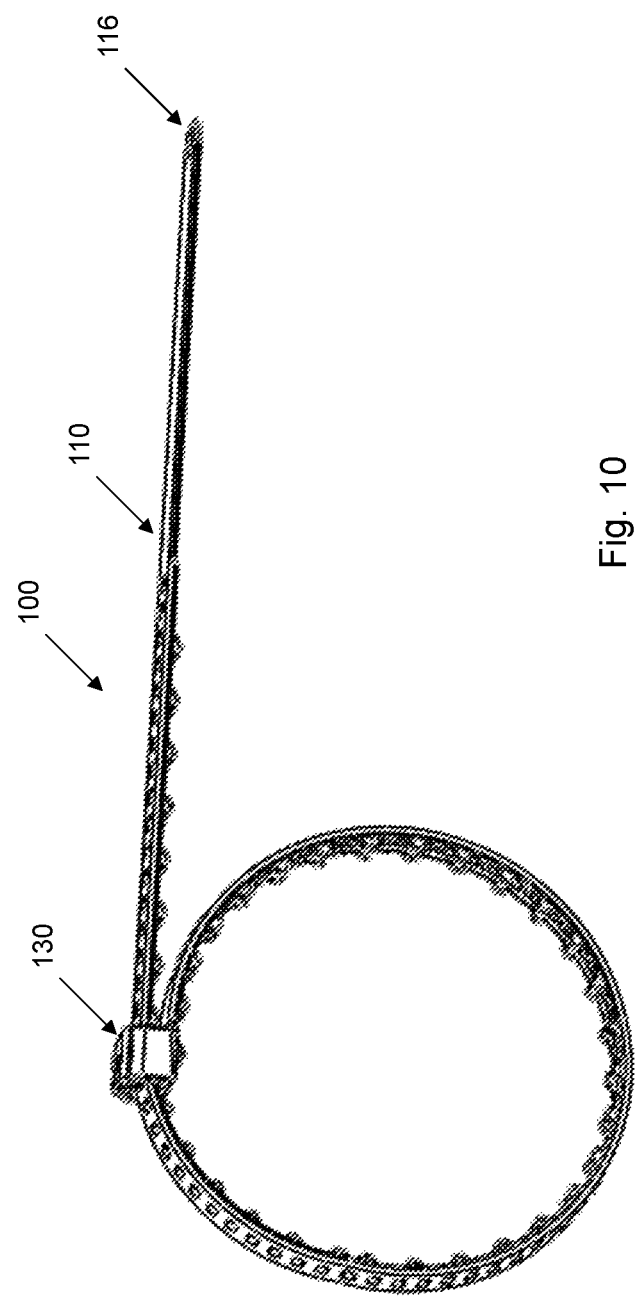
FIG. 10 illustrates a medical device with the band inserted through the locking case forming a band loop.

The perforations 120 and rungs 122 are arranged on at least the portion of the band 110 that is closest to the trailing end 118 and the locking case 130. As a consequence, the perforations 120 and rungs 122 can start at the trailing end 118 or the locking case 130 or close to the trailing end 118 or the locking case 130 and run at least a distance up through the band length towards the leading end 116. It is actually possible to have perforations 120 and rungs 122 along the whole length of the band 110 but for most practical applications it is sufficient to have the perforations 120 and rungs 122 up to a sub-part of the band length as shown in FIGS. 1 and 13. In this context, the important feature is that the perforations 120 and rungs 122 should be provided at least up to a portion of the band length towards the leading end 116 to engage a locking member 140, such as arranged in the locking case 130, when the leading end 116 is fed into the channel 150 and the band 110 forms a loop, see FIG. 10, around a structure, for instance around a tissue or fractured bone. Thus, the largest diameter of the loop when the locking member 140 first starts engaging with the perforations 120 and rungs 122 as the leading band end 116 is pulled through the channel 150 should preferably be larger than the outer diameter of any structure, such as bone or tissue, present in the loop. For most practical applications, the perforations 120 and rungs 122 could therefore extend over a length of the band 110 that is from about one or few centimeters up to several centimeters.

The perforations 120 and rungs 122 can, in a first embodiment, be realized as an array of through-holes or apertures 120 through the band 110 as illustrated in FIGS. 6-8. These holes 120 form, together with the intermediate band material, i.e. rungs 122, a ladder structure that can be engaged by the locking member 140 to achieve the reverse-motion brake. In a second embodiment, the perforations 120 and rungs 122 are instead a plurality of notches in the rear side 114 or the front side 112 of the band 110. These notches, thus, form indentations in the band 110 but not necessarily penetrate through the whole thickness of the band 110 as in the first embodiment. The intermediate band material between the notches then corresponds to the rungs 122. A third embodiment is to replace the holes or notches with a plurality of protruding members, such as ratchet teeth forming the rungs 122, extending a short distance from the front or rear side surface. Also changes or alternations in the topography of the surface of the rear side 114 or the front side 112 of the band 110 in order to allow engagement with the locking member 140 could be used as perforations 120 and rungs 122 according to an embodiment.

The locking member 140 could be in the form of at least one lock tooth or latching element dimensioned to interlock perforations 120 and rungs 122 defined in the band 110. In the case of hole- or notch-implemented perforations 120 and rungs 122, the locking member 140 is arranged for step-by-step protrusion into the holes or notches as the band 110 is being fed through the channel 150. Correspondingly, the locking member 140 engages with the protrusion of a ratchet teeth solution as the band 110 is being pulled through the channel 150 in the locking case 130.

The inter-engagement between the locking member 140 and the perforations 120 and rungs 122 permits forward movement of the band 110 through the channel 150 but restrains the band 110 against reverse movement through the channel 150, thereby achieving a reverse-motion brake.

In an embodiment as shown in FIGS. 5 and 11, the locking case 130 comprises the locking member 140 disposed in connection with the channel 150, which is running through the locking case 130 and is dimensioned for reception of the band 110.

The locking member 140 preferably ramps upward from the entrance side to the exit side of the channel 150, while the opposite face of the locking member 140 drops vertically, see FIG. 11. It is anticipated by the present embodiments that the locking member 140 may include multiple locking teeth, such as repeatedly positioned in series or multiples in connection with, preferably in, the channel 150.

The locking member 140 preferably has a base portion that is fully attached to a wall 151 of the channel 150 in the locking case 130. This means that the locking member 140 forms a rigid structure with a solid attachment to the locking case 130. Hence, in a particular embodiment the locking member 140 is substantially inflexible and is preferably configured to maintain a rigid configuration when the band 110 is being pulled through the channel 150.

The locking member 140 is disposed in connection with the channel 150 and is preferably provided somewhere along the length of the channel 150. Alternatively or in addition, the locking member 140 could be provided in connection with the entrance and/or exit of the channel 150 in the locking case 130 or indeed outside of the locking case 130, which will be further discussed here below in connection with FIGS. 3 and 4.

The locking member 140 can be situated in connection with the inner wall 151 of the locking case 130 that is on the same side of the channel 150 as the band 110. The perforations 120 and rungs 122 are then provided on at least the rear side 114 of the band 110. Alternatively, the locking member 140 is provided on the inner wall opposite to the side of the channel 150 at which the band 110 is anchored to the locking case 130. The perforations 120 and rungs 122 are then provided on at least the front side 112 of the band 110.

As is shown in FIGS. 6-8, the perforations 120 and the rungs 122 are preferably arranged in a central portion 111 of the band 110 with regard to a width or transversal extension of the band 110. In such a case, the multiple studs 160, 162 are preferably arranged on respective peripheral portions 113, 115 of the rear side 114 of the band 110 with regard to the width extension.

In an embodiment, the multiple studs 160, 162 are arranged as multiple pairs 164 of studs 160, 162 with a first stud of each respective pair 164 arranged on a first peripheral portion 113 of the rear side 114 of the band 110 and a second stud 162 of each respective pair 164 arranged on a second peripheral portion 115 of the rear side 114 of the band 110. Hence, in an embodiment the studs 160, 162 are arranged on either side of the centrally, with regard to the width extension, positioned perforations 120 and rungs 122 on the band 110.

In FIG. 6, each pair 164 of studs 160, 162 is substantially aligned with a respective rung 122 in the band 110. In an alternative variant, each pair 164 of studs 160, 162 could be aligned with a respective perforation 120 in the band 110.

Generally, it is not necessary to have such a pair 164 of studs 160, 162 in connection with each rung 122 or perforation 120 in the band 110. FIG. 8 illustrate a variant where the pair 164 of studs 160, 162 is aligned with every second rung 122 in the band 110. This concept can be generalized to have each pair 164 of studs 160, 162 aligned with every $n^{th}$ rung 122 or perforation 120 in the band 110 for some defined integer value of n.

The first stud 160 and the second stud 162 in each pair 164 could be slightly displaced with regard to each other along the longitudinal extension of the band 110 as shown in FIG. 7. In the particular example shown in this figure, the first stud 160 in the pair 164 is aligned with a rung 122 whereas the second stud 162 in the pair 164 is, in this illustrative example, aligned with a perforation 120 in the band 110. This should, however, merely be seen as an illustrative example of the general embodiment of having studs 160, 162 in the pair 164 longitudinally displaced relative to each other.

The multiple studs 160, 162 are arranged on at least the portion of the band 110 that is closest to the trailing end 118 and the locking case 130. As a consequence, the studs 160, 162 can start at the trailing end 118 or the locking case 130 or close to the trailing end 118 or the locking case 130 and run at least a distance up through the band length towards the leading end 116. It is actually possible to have the studs 160, 162 along the whole length of the band 110 but for most practical applications it is sufficient to have the studs 160, 162 up to a sub-part of the band length as shown in FIG. 1.

In an embodiment, the studs 160, 162 are preferably provided on at least the portion of the band 110 at which the perforations 120 and rungs 122 are provided. The studs 160, 162 may in addition be provided on the rear side 114 of the band 110 in connection with the locking case 130 as shown in FIG. 2.

Hence, in an embodiment the multiple studs 160, 162 are arranged on at least a portion of the rear side 114 of the band extending from the locking case 130 up to a distance towards the leading end 116 of the band 110. The channel 150 through the locking case 130 then preferably comprises at least one stud portion 156, 158 dimensioned and arranged in the locking case for reception of the multiple studs 160, 162, see FIGS. 5 and 12.

In an embodiment, the locking member 140 is connected to the locking case 130 and is disposed in connection with the channel 150. The channel 150 then preferably comprises a first stud portion 156 and a second stud portion 158 with the locking member 140 arranged between the first stud portion 156 and the second stud portion 158.

Thus, in these embodiments the channel 150 comprises at least one, preferably two, stud portions 156, 158 to allow the studs 160, 162 to pass through the channel 150 and the locking case 130 when the leading end 116 and the band 110 is pulled through the channel 150. If the studs 160, 162 are arranged on peripheral portions 113, 115 of the rear side 114 of the band 110 as shown in FIGS. 6-8, the stud portions 156, 158 are preferably provided on either side of the central locking member 140 to allow the studs 160, 162 to pass through the stud portions 156, 158 when the band 110 is pulled through the channel 150 and the locking member 140 engages and interlocks the perforations 120 and the rungs 122 in the band 110.

The multiple studs 160, 162 protrude away from the surface of the rear side 114 of the band 110. The multiple studs 160, 162 can be designed according to various embodiments. For instance, the studs 160, 162 could each have a sharp point or tip, in particular if a tissue engaging action is desired. Alternatively, the studs 160, 162 could have rounded surface, a flat or squared surface or indeed shapes in between or combining said or similar designs. The studs 160, 162 could have small protrusions, such as microstuds on studs 160, 162, on their surface, providing additional grip and/or elevation.

The line of studs 160, 162 on each peripheral side of the band 110 is not necessarily restricted to a single line of protrusions on each side, paired or multiple studs 160, 162 on each side could be designed.

The studs 160, 162 could be arranged in parallel, positioned straight opposite on each side or dislocated from the opposite position, thus forming a zigzag pattern, or the positioning could be any other random placement which does not interfere with the locking mechanism or passage through locking case 130.

As discussed above and shown in FIGS. 5 and 12 the locking member 140 is preferably connected to the locking case 130 and provided in the channel 150 through the locking case 130.

In an alternative embodiment, at least one locking member 142, 144 could be provided outside of the locking case 130. Hence, in an embodiment the locking case 130 is arranged on the front side 112 of the band 110 at a distance from the trailing end 118 of the band 110, see FIG. 3. The locking member 142, 144 is arranged on the front side 112 of the band 110 at a position between the trailing end 118 of the band 110 and the locking case 130.

Thus, in this embodiment the locking member 142, 144 does not necessarily have to be provided in the locking case 130 but is rather provided closer to the trailing end 118 of the band as compared to the locking case 130. In such embodiment, one locking member 142 could be positioned outside of the locking case 130. Alternatively, multiple, i.e. at least two, locking members 142, 144 could be positioned outside of the locking case 130 as shown in FIG. 3.

This means that a second locking member 142 is arranged on the front side 112 of the band 110 at the position between the trailing end 118 of the band 110 and the locking case 130. In an optional embodiment, a third locking member 144 is arranged on the front side 112 of the band at a position between the second locking member 142 and the locking case 130.

The above disclosed embodiment of using at least one locking member 142, 144 outside of the locking case 130 can be combined with having a locking member 140 connected to the locking case 130. In such an embodiment, the medical device 100 comprises a first locking member 140 connected to the locking case 130 and disposed in connection with the channel 150. The medical device 100 also comprises a second locking member 142 arranged on the front side 112 of the band 110 at a position between the trailing end 118 of the band 110 and the locking case 130. In an optional embodiment, the medical device 100 may comprise an optional third locking member 144 arranged on the front side 112 of the band 110 at a position between the second locking member 142 and the locking case 130.

The usage of at least two locking members 140, 142, 144 implies redundancy in the locking of the band 110. This further implies that any risk of the band 110 moving backwards through the channel 150 in the locking case 130 due to a malfunction in the interlocking of the locking member 140 to the perforations 120 and rungs 122. This means that if one of the locking members 140, 142, 144 would malfunction, such as due to a damage thereof, the medical device 100 is still kept locked around the intended structure, such as bone or tissue, due to the action of the at least one additional locking member 140, 142, 144.

In connection with pulling the band 110 through the channel 150 in the locking case 130 the band 110 could be displaced slightly from the trailing band portion so that the second and/or third locking member 142, 144 cannot engage and interlock perforations 120 and rungs 122 defined in the band 110. Hence, it could be possible that band 110 unintentionally runs alongside of the second and/or third locking member 142, 144 instead of over the second and/or third locking member 142, 144.

Such a problem could be solved by having a guiding case 132 as shown in FIG. 4. Hence, in such an embodiment, the medical device 100 comprises a guiding case 132 arranged on the front side 112 of the band 110 at the trailing end 118 of the band 110 or at a position between the locking member 142, 144, i.e. the second locking member 142 or the second and third locking member 142, 144, and the trailing end 118 of band 110. The guiding case 132 has a channel 134 dimensioned for reception of the band 110.

As shown in FIG. 4, the second locking member 142 and, if present, the third locking member 144 are positioned on the front side 112 of the band 110. In such a case, the second and optional third locking member 142, 144 may be arranged at position(s) between the locking case 130 and the guiding case 132. Alternatively, an optional locking member 142 could be arranged in connection with the guiding case 132 and another locking member 144 arranged on the front side 112 of the band 110 at a position between the locking case 130 and the guiding case 132. The leading end 116 of the band 110 is then first entered into the channel 134 of the guiding case 132 and is then pulled over the locking member(s) 142, 144 and entered into the channel 150 of the locking case 130. The guiding case 132 and the locking case 130 will then maintain the band 110 running correctly over the locking member(s) 142, 144 and prevent the band 110 from being displaced from the locking member(s) 142, 144. As a consequence, an efficient interlocking of perforations 120 and rungs 122 in the band 110 will occur with the locking member(s) 142, 144.

The guiding case 132 can be in the form of a simple case or housing with a channel 132, aperture or through-hole that is dimensioned for reception of the band 110 including the studs 160, 162 present on the rear side 114 of the band 110.

In another embodiment, the guiding case 132 could be in the form of a second locking case then basically having dual functions. Thus, firstly the guiding case 132 restricts the band 110 from running alongside the locking member(s) 144. Secondly, the guiding case 132 could be equipped with a locking member 142 configured to interlock perforations 120 and rungs 122 defined in the band 110. In such a case, this locking member 142 is connected to the guiding case 132 and is disposed in connection with the channel 134 running through the guiding case 132. In this embodiment, the guiding case 132 and the locking case 130 have substantially a same design and function.

Various embodiments of the medical device 100 may, thus, have different numbers of locking members 140, 142, 144. For instance, a single locking member 140 could be arranged connected to the locking case 130 and disposed in connection with the channel 150 therethrough. Alternatively, a single locking member 142 could be arranged on the front side 112 of the band 110 at a position between the trailing end 118 of the band 110 and the locking case 130.

If the medical device 100 comprises two locking members 140, 142, a first locking member 140 is preferably connected to the locking case 130 and disposed in connection with the channel 150, whereas a second locking member 142 is arranged on the front side 112 of the band 110 at a position between the trailing end 118 of the band 110 and the locking case 130. Alternatively, both locking members 142, 144 could be arranged on the front side 112 of the band 110 at respective positions between the trailing end 118 of the band 110 and the locking case 130.

Correspondingly, if the medical device 100 comprises three locking members 140, 142, 144, a first locking member 140 is preferably connected to the locking case 130 and disposed in connection with the channel 150, whereas a second and a third locking member 142, 144 are arranged on the front side 112 of the band 110 at a respective position between the trailing end 118 of the band 110 and the locking case 130. Alternatively, one locking member 142 could be connected to the guiding case 132 and disposed in connection with the channel 134 running therethrough.

The medical device 100 may also comprise more than three locking members 140, 142, 144, of which at least one is preferably arranged in connection with the locking case 130 and the remaining being arranged between the trailing end 118 of the band 110 or the guiding case 132 and the locking case 130 or in connection with the guiding case 132 and between the guiding case 132 and the locking case 130.

In an embodiment, the medical device 100 comprises multiple locking members 140, 142, 144 as discussed herein but does not necessarily have any studs arranged on the rear side 114 of the band 110. Hence, another aspect of the embodiments relates to a medical device 100 comprising an elongated, flexible band 110 having a front side 112, a rear side 114, a leading end 116 and a trailing end 118, and having perforations 120 and rungs 122 defined therein. The medical device 100 also comprises a locking case 120 connected to the front side 112 of the band 110 and having a channel 150 dimensioned for reception of the band 110. The medical device 100 further comprises a first locking member 140 connected to the locking case 130 and disposed in connection with the channel 150 and configured to interlock perforations 120 and rungs 122 defined in the band. The medical device 100 additionally comprises a second locking member 144 arranged on the front side 112 of the band 110 at a position between the trailing end 118 of the band 110 and the locking case 130.

The medical device according to this another aspect preferably comprises the previously described guiding case 132.

A further aspect of the embodiments relates to a medical device 100 comprising an elongated, flexible band 110 having a front side 112, a rear side 114, a leading end 116 and a trailing end 118, and having perforations 120 and rungs 122 defined therein. The medical device 100 also comprises a locking case 130 connected to the front side 112 of the band 110 and having a channel 150 dimensioned for reception of the band 110. The locking case 130 is arranged on the front side 112 of the band 110 at a distance from the trailing end 118 of the band 110. The medical device 100 further comprises a locking member 142, 144 arranged on the front side 112 of the band 110 at a position between the trailing end 118 of the band 110 and the locking case 130. The medical device 100 additionally comprises a guiding case 132 arranged on the front side 112 of the band 110 at the trailing end 118 of the band 110 or at a position between the locking case 130 and the trailing end 118 of the band 110. The guiding case 132 has a channel 134 dimensioned for reception of the band 110.

The medical device according to this further aspect preferably comprises a second locking member 140 connected to the locking case 130 and disposed in connection with the channel 150.

The medical device 100 according to the another and/or further aspect may have additional locking members 144 as discussed above. For instance, the guiding case 132 of the medical device 100 is arranged on the front side 112 of the band 110 at a position between the locking member 142, 144 and the trailing end 118 of the band 110. In such a case, the medical device 100 may further comprise a third locking member 144 arranged on the front side 112 of the band 110 at a position between the locking member 142 and the locking case 130. Alternatively, or in addition, the medical device 100 comprises a third locking member 142 arranged in connection with the guiding case 132, such as disposed in connection with the channel 134 of the guiding case 132.

Additional locking members provide improved mechanical properties, greater strength of the medical device. In addition, an additional locking case provides guidance of locking member into receiving perforations, thereby ensuring that the flexible band and its perforations are correctly aligned to the locking member(s).

In an embodiment, the channel 150 through the locking case 132 comprises, as is more clearly shown in FIG. 5, an arcing portion 152 that constitutes the portion of the channel 150 that is substantially opposite to the locking member 140. This arching portion 152 enables the band 110 to arch over the locking member 140 when the locking member 140 is aligned with and engages a rung 122 in the band 110.

Hence, when the locking member 140 engages a rung 122 in the band 110 the locking member 140 pushes at least a central part (with regard to a width or transversal extension of the band 110) of the band 110 into the arching portion 152 of the channel 150. Thus, according to a particular embodiment the locking member 140 is preferably rigid enough not to spring or swing back when engaging a rung 122 in the band 110 but in clear contrast pushes on the band 110 to force the portion of the band 110 aligned with the locking member 140 to protrude at least partly into the arching portion. Thus, in an embodiment, the locking member 140 is rigidly arranged on a wall 141 of the channel 150 in the locking case 130 and is preferably substantially inflexible and is configured to maintain a rigid configuration when the band 110 is being pulled through the channel 150.

When the band 110 is pulled a bit further through the channel 150 so that the locking member 140 now becomes aligned with a perforation 120, the locking member 140 will protrude at least partly into the perforation 120, see FIG. 12. At this point the locking member 140 does no longer push against the band 110. Hence, the band 110 will move or spring back into a basal portion 154 of the channel 150 and thereby no longer protrude into the arching portion 152. This basal portion 154 preferably comprises the portion of the channel 150 that faces the locking member 140.

When the band 110 is being pulled through the channel 150 the band 110 preferably alternates between extending substantially in the basal portion 154 when the locking member 140 is aligned with and protrudes into a perforation 120 of the band 110 and protruding at least partly into the arching portion 152 when the locking member 140 is aligned with and engages a rung 122 of the band 110.

When the band 110 is extending substantially in the basal portion 154, a portion of the band 110 present in the channel 150 has basically a flat cross-sectional configuration with regard to a cross-section along the transversal extension of the band 110, see FIG. 12. The cross-sectional configuration will, hence, typically correspond to a rectangular (assuming that the thickness of the band 110 is smaller than the width of the band 110). However, when the band 110 protrudes at least partly into the arching portion 152, the portion of the band 110 present in the channel 150 typically has an arched cross-sectional configuration. The cross-sectional configuration will, hence typically correspond to an arch or arc.

The basal portion 154 and the arching portion 152 preferably have different extensions along the width of the locking case 130. In particular, the basal portion 154 preferably has a wider extension as compared to the arching portion 152. This means that the basal portion 154 could be viewed as a slot through the locking case 130 and with the arching portion 152 present at a central (with regard to the extension along the width of the locking case 130) part of the basal portion 154. The extension of the basal portion 154 preferably corresponds to or is slightly wider than the width of the band 110, whereas the extension or width of the basal portion 152 is preferably narrower than the width of the band 110. Hence, when the band 110 is moved through the channel 150 and the locking member 140 is aligned with and engages a rung 122 of the band 110, the central (with regard to the width of the band 110) part of the band 110 is pushed into the arching portion 152. The peripheral (with regard to the width of the band 110) parts of the band 110 are, however, preferably still present in the basal portion 154 since there is not room for the complete band 110 to be moved from the basal portion 154 to the arching portion 152. When the locking member 140 is aligned with and protrudes into a next perforation 120 of the band 110 the central part of the band 110 is moved back towards the basal portion 154 so that the complete part of the band 110 present in the channel 150 is preferably in the basal portion 154.

In a preferred embodiment, the band 110 automatically engages the locking member 140 when the locking member 140 is aligned with a perforation 120 in the band 100. Thus, when given the chance the band 110 will leave the arched configuration, which is a stressed and energy-dependent position, and level out once the band 110 is moved from a position with the locking member 140 aligned with a rung 122 to the locking member 140 aligned with a perforation 120 in the band 110.

The above described design of the channel 150 through the locking case 130 is in particular suitable in connection with a rigid and substantially inflexible locking member 140 disposed in the locking case 130. Alternatively, a flexible locking member 140 could be used that is allowed to move back and forth as the band 110 is pulled through the channel 150. In such a case, the channel 150 does not need to have any arching portion and basal portion but could rather be designed to allow the band 110 with the studs 160, 162 to move through the channel 150.

In order to simplify handling of the medical device 100 and in particular simplify entering the leading band end 116 into the channel 150 in the locking case 130 and optionally into the channel 134 in the guiding case 132 using a single hand, an intermediate portion of the band 110 between the leading end 116 and the trailing end 118 is optionally bent. A preferred embodiment has a U-shaped intermediate portion to position the leading end 116 close to the locking case 130 or the guiding case 132 even when the band 110 has not yet been introduced into the channel 150 or the channel 134.

Due to the U-shape of the intermediate band portion, a medical person positions the structure, such as fractured bone or tissue, in the space formed between the two, almost parallel, band portions between the trailing end 118 and the intermediate portion and the leading end 116 and the intermediate portion. At this position, the medical person can, using one hand, introduce the leading band end 116 into the channel 150 or the channel 134 and pull the band 110 therethrough.

In a typical embodiment, the medical device 100 is manufactured as a single piece, for instance by molding the medical device 100 in a suitable polymer material. In an alternative embodiment, the locking case 130 and the locking member 140 are manufactured, such as molded, as a single piece and with the band 110 as another single piece. These two pieces can then be attached together, for instance by gluing or fused together in another way. In a further embodiment, a two-component injection molding machine or equipment could be used to manufacture the medical device 100. In such a case, a first polymer material can be used for the solid band 110 and a second, different polymer material is used for the locking case 130, the locking member 140 and the perforated part of the band 110. In this approach, polymer materials with different properties can be used for the different pieces. For instance, a non-resorbable, cheaper polymer material could be used for the solid band 110, whereas a resorbable, typically more expensive polymer material could be used for the locking case 130, the locking member 140 and the perforated part of the band 110.

In an embodiment, the solid part of the flexible band 110 and outermost part of the flexible band 110 with perforations will not be left in the patient but is rather cut off and removed during the surgical procedure. Thus, the end of the flexible band 110 is removed and could therefore be made in any (non-toxic) material.

The whole medical device 100 could be non-resorbable if the medical person preferably restricts the time of the medical device 100 in the patient, i.e. short-term use, not left permanently in the body. For those skilled in the art it will be known that implants that are non-resorbable are used in clinical practice and are licensed to be left permanently. The medical device 100 described here could therefore be made in a non-resorbable material although resorbable materials may be preferred.

The material of the medical device 100 is a biocompatible material, which does not have any major toxic or injurious effects on the animal or human body. Examples of such biocompatible materials include hypoallergenic materials traditionally employed for implantable medical devices. Currently preferred materials include biocompatible polymer materials and in particular resorbable or bio-absorbable polymers.

Examples of such resorbable polymers that can be used according to the embodiments include polyglycolide, poly-L-lactide, poly-p-dioxanone, poly(trimethylene carbonate), polycaprolactone and copolymers derived from two or more monomers selected from glycolide, L-lactide, p-dioxanone, trimethylene carbonate and $\epsilon$-caprolactone.

However, also other monomers could be used to form resorbable polymers or copolymers, for instance, $\delta$-valerolactone, $\beta$-butyrolactone, $\epsilon$-decalactone, 2,5-diketomopholine, pivalolactone, $\alpha$-diethylpropiolactone, ethylene carbonate, ethylene oxalate, 3-methyl-1,4-dioxane-2,5-dione, 3,3-diethyl-1,4-dioxan-2,4-dione, $\gamma$-butyrolactone, 1,4-dioxepan-2-one, 1,5-dioxepan-2-one, 1,4-dioxan-2-one, 6,8-dioxabicycloctane-7-one, and combinations thereof. Further suitable resorbable materials that can be used according to the present invention are described in U.S. Pat. Nos. 4,968,317 and 4,898,186, the teachings of which regarding resorbable, biocompatible materials is hereby incorporated by reference.

Resorbable materials imply that the medical device 100 can be left in the animal or human body and are resorbed by the body following a time after the surgical procedure. Thus, an advantage of using a resorbable medical device 100 is that the tissue response is restricted and limited in extent and time and no further surgical procedure is required for removing the medical device 100 after the operation has been completed and the fractured bone or ligated tissue has healed. This saves both costs and suffering from the relevant human or animal patient. The use of resorbable materials significantly reduces or removes the risk of chronic tissue reactions, thereby reducing the risk that the implant needs to be prematurely removed.

The design of the medical device 100 and in particular of the channel 150 with its arching portion 152 and rigid locking member 140 is in particular suitable for usage with resorbable polymer materials. A reason for this is that such resorbable polymer materials may be softer as compared to non-resorbable polymer materials. This means that using a traditional approach with a locking member springing and swinging up and down as the band is being pulled through the channel of the locking case might not be possible due to the softness and thereby lack of springing effect of the resorbable polymer material. This means that the design of the medical device 100 according to the embodiments enables usage of polymer materials that are not suitable or even possible to use in connection with prior art designs of cable ties.

Although the medical device 100 is preferably made of a polymer material also non-polymeric or non-plastic materials, such as metal materials or metal alloy materials, such as titanium, titanium alloys and stainless steel, can be used as long as the band material is flexible enough to allow being bent when pulling the leading end 116 of the band 110 through the channel 150 in the locking case 130.

The actual size of the medical device 100 is not decisive for the teachings of the present embodiments and can be selected based on the particular application, animal/human subject and/or tissue to be ligated.

However, in most typical implementations, the length of the band 110 could be from about one or few centimeters to one or more decimeters, with a thickness from the range of sub-millimeters to one or more millimeters and a width from the range of sub-millimeters to one or more millimeters. The width and/or thickness of the band 110 must not necessarily be uniform. In clear contrast, the leading end 116 could be narrower and/or thinner than the trailing end 118 to thereby facilitate insertion of the leading end 116 into the channel 150. Correspondingly, the length of the band portion from the leading end 116 up to the intermediate portion could be somewhat longer than the band portion from the trailing end 118 up to the intermediate portion. This prevents the leading end 116 from easily dropping out of the locking case 130 once introduced into the channel 150.

FIG. 9 is a flow diagram illustrating various methods that involve usage of the medical device according to the embodiments.

In a first embodiment, the method is a method of stabilizing a bone fracture. The method starts in step S1, which comprises inserting a leading end of a band of a medical device according to the embodiments into a channel of a locking case of the medical device to form a loop around a fractured bone. A next step S2 comprises pulling the leading end of the band through the channel to lock the band around the fractured bone. Multiple studs arranged on a rear side of the band elevate the medical device from a surface of the fractured bone to reduce a risk of the medical device restricting microcirculation in periosteum of the fractured bone.

The medical device thereby provides a safe and efficient stabilization of a fractured bone while preserving vascularity and microcirculation in the periosteum and also the cortex of the fractured bone.

In an alternative embodiment, FIG. 9 discloses a tissue ligation method. The method starts in step S1, where a leading end of a band of a medical device according to the embodiments is inserted into a channel of a locking case of the medical device to form a loop around a tissue to be ligated. Finally, the leading end of the band is pulled through the channel to lock the band around the tissue and achieve a tissue ligation. Multiple studs arranged on a rear side of the band engage the tissue to reduce a risk of the medical device slipping off the tissue.

In a further embodiment, FIG. 9 discloses a purse-string suturing method. The method starts in step S1, where a leading end of a band of a medical device according to the embodiments is inserted into a channel of a locking case of the medical device to form a loop encircling an opening of a tissue. Finally, the leading end of the band is pulled through the channel to lock the band around and closing the opening of the tissue. Multiple studs arranged on a rear side of the band engage the tissue to reduce a risk of the medical device slipping off the tissue.

The design of the medical device allows the leading end to be pulled using a single hand operation, thereby leaving the other hand free to remove surrounding tissue that must not be ligated. Due to the inter-engagement of the perforations and rungs and the locking member(s), the band is prevented from reverse movement and opening of the ligation loop.

The medical device can be used for ligating vastly varying tissues in both human and animal, preferably mammalian animal bodies. Non-limiting examples include ligation of blood vessels, such as veins and arteries, for instance during laparoscopy; fallopian tube ligation/tubal ligation; uterine horn; uterine body or testicular funicle, for instance during ovariohysterectomy and castration; during spleen ectomy or intestinal, pulmonary or cardiac procedures. Other non-limiting examples include compression of typically vascular tissue and the consequent prevention of bleeding when performing partial nephrectomy/kidney resection, removal of lung lobes, liver or spleen resection or intestinal surgery or similar situations obvious for those skilled in the art. The medical device can also be used in any soft tissues surgery, in or outside the abdominal or thoracic cavity, where a ligation is desired. The medical device can therefore be utilized instead of traditional ligatures but also replace devices such as stapling equipment, ultrasonic scalpels, vessel sealing devices, transfixation ligatures, surgeons knot and other knots, e.g. Miller's knot. The medical device may be used to close tubular tissue structures, non-limiting examples include closing intestinal tissue around the instruments anvil and trocar used for circular stapling in anastomosis (re-joining) of the tissue.

It is anticipated that any surplus band portion extending beyond the channel exit in the locking case after fully pulling the band tight around the tissue can be cut off by the medical person.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A medical device comprising:
an elongated, flexible band having a front side, a rear side, a leading end and a trailing end, and having perforations and rungs defined therein;
a locking case arranged on said front side of said band and having a channel dimensioned for reception of said band;
a locking member configured to interlock perforations and rungs defined in said band, wherein said locking member is connected to said locking case and disposed in connection with said channel; and
multiple pairs of studs arranged on said rear side of said band, with a first stud of each respective pair arranged on a first peripheral portion with regard to a width extension of said band and a second stud of each respective pair arranged on a second peripheral portion with regard to the width extension of said band,
wherein said channel comprises a first stud portion and a second stud portion dimensioned and arranged in said locking case for reception of said multiple studs, with said locking member arranged between said first stud portion and said second stud portion.

2. The medical device according to claim 1, wherein said locking case is arranged on said front side of said band at a distance from said trailing end of said band.

3. The medical device according to claim 2, further comprising:
a second locking member arranged on said front side of said band at a position between said trailing end of said band and said locking case.

4. The medical device according to claim 3, further comprising a third locking member arranged on said front side of said band at a position between said second locking member and said locking case.

5. The medical device according to claim 2, further comprising a guiding case arranged on said front side of said band at said trailing end of said band or at a position between said locking member and said trailing end of said band, said guiding case having a channel dimensioned for reception of said band.

6. The medical device according to claim 1, wherein said channel comprises an arching portion arranged opposite to said locking member and a basal portion facing said locking member; and
said band is configured to arch over said locking member and protrude at least partly into said arching portion when said locking member engages a rung of said band and to extend in said basal portion when said locking member protrudes into a perforation of said band.

7. The medical device according to claim 6, wherein said locking member is rigidly arranged on a wall of said channel in said locking case.

8. The medical device according to claim 6, wherein said locking member is substantially inflexible and is configured to maintain a rigid configuration when said band is being pulled through said channel.

9. The medical device according to claim 1, wherein said perforations and rungs are defined in a central portion of said band with regard to the width extension of said band.

10. The medical device according to claim 1, wherein said multiple studs are arranged at least on a portion of said rear side of said band extending from said locking case up to a distance towards said leading end of said band.

11. A tissue ligation method comprising:
inserting a leading end of a band of a medical device according to claim 1 into the channel of the locking case of said medical device to form a loop around a tissue; and
pulling said leading end of said band through said channel to lock said band around said tissue and achieve a tissue ligation, wherein the multiple studs arranged on a rear side of said band engage said tissue to reduce a risk of said medical device slipping off said tissue.

12. A method of stabilizing a bone fracture comprising:
inserting a leading end of a band of a medical device according to claim 1 into the channel of the locking case of said medical device to form a loop around a fractured bone; and
pulling said leading end of said band through said channel to lock said band around said fractured bone, wherein the multiple studs arranged on a rear side of said band elevate said medical device from a surface of said fractured bone to reduce a risk of said medical device restricting microcirculation in periosteum of said fractured bone.

13. A purse-string suturing method comprising:
inserting a leading end of a band of a medical device according to claim 1 into the channel of the locking case of said medical device to form a loop encircling an opening of a tissue; and
pulling said leading end of said band through said channel to lock said band around and closing said opening of said tissue, wherein the multiple studs arranged on a rear side of said band engage said tissue to reduce a risk of said medical device slipping off said tissue.

* * * * *

UNITED STATES PATENT AND TRADEMARK OFFICE
CERTIFICATE OF CORRECTION

PATENT NO. : 10,004,536 B2
APPLICATION NO. : 15/325186
DATED : June 26, 2018
INVENTOR(S) : Odd Höglund et al.

It is certified that error appears in the above-identified patent and that said Letters Patent is hereby corrected as shown below:

On the Title Page

Item [30]:
Foreign Application Priority Data, change "1450890" to --1450890-7--.
Foreign Application Priority Data, change "1550175" to --1550175-2--.

Signed and Sealed this
Eighteenth Day of September, 2018

Andrei Iancu
*Director of the United States Patent and Trademark Office*